United States Patent [19]

Kim et al.

[11] Patent Number: 5,961,965
[45] Date of Patent: Oct. 5, 1999

[54] WATER-SOLUBLE OR WATER-DISPERSIBLE POLYASPARTIC ACID DERIVATIVES THEIR PREPARATION AND THEIR USE

[75] Inventors: Son Nguyen Kim, Hemsbach; Axel Sanner, Frankenthal; Peter Hössel, Schifferstadt; Matthias Kroner, Eisenberg, all of Germany

[73] Assignee: BASF Aktiengesellschaft, Ludwigshafen, Germany

[21] Appl. No.: 08/886,287

[22] Filed: Jul. 1, 1997

[30] Foreign Application Priority Data

Aug. 2, 1996 [DE] Germany ............................ 196 31 379

[51] Int. Cl.⁶ ............................. A61K 7/11; C08G 69/10
[52] U.S. Cl. ..................................... 424/70.17; 424/78.03; 424/DIG. 1; 525/424; 528/328; 528/263; 544/141; 544/372; 546/208
[58] Field of Search ............................. 424/70.17, 78.03; 528/328, 363; 525/420; 544/372, 141; 546/208

[56] References Cited

U.S. PATENT DOCUMENTS 3,846,380  11/1974  Fujimoto ............................... 260/78 A
4,735,797  4/1988  Grollier ..................................... 424/47
4,745,161  5/1988  Saudek et al. .......................... 525/420
5,175,285  12/1992  Lehmann ................................ 544/141

FOREIGN PATENT DOCUMENTS 767 191   4/1997  European Pat. Off. .
2403076   5/1979  France .
2424292   11/1979 France .
2005705   4/1979  United Kingdom .

OTHER PUBLICATIONS

Derwent Publications Ltd., Section Ch, Week 9440, Class A23, AN 94–322255, XP002045386 (English abstract of JP 6248072A; Sep. 6, 1994).

Neuse et al., *die Angewandte Makromol. Chemie.*, vol. 192, No. 3300, 1991, pp. 35–50.

*Primary Examiner*—Evelyn Huang
*Attorney, Agent, or Firm*—Keil & Weinkauf

[57] ABSTRACT

A description is given of water-soluble or water-dispersible polyaspartic acid derivatives, their preparation and their use in cosmetology, especially in hair cosmetology.

18 Claims, No Drawings

WATER-SOLUBLE OR WATER-DISPERSIBLE POLYASPARTIC ACID DERIVATIVES THEIR PREPARATION AND THEIR USE

The present invention relates to water-soluble or water-dispersible polyaspartic acid derivatives, to their preparation and to their use in cosmetology.

Synthetically produced polyamino acids and their derivatives have been known for a long time and on the basis of their biological compatibility are used, for example, for special applications in medicine and pharmacy. Apart from peptides having an effect-specific sequence, such compounds are principally film-forming substances for improving the handling properties of pharmaceutical preparations, for improving their storage stability and, in particular, for influencing the rate of release of the active substances. In these applications use is made, for example, of polymers of individual amino acids, such as polyaspartic acid, polyglutamic acid and polylysine, and also of copolymers and biologically well-compatible derivatives of such polyamino acids.

DE-A-37 00 128 describes poly(hydroxyalkyl) aminodicarboxylic acid derivatives having biologically inactive acyl groups, processes for their preparation and their use for depot preparations with controlled release of active substance.

DE-A-36 12 102 describes soluble and biodegradable copolymers comprising aspartic and/or glutamic acid units and containing reactive groups, for example hydrazide or azide groups, for the chemical attachment of biologically active substances.

EP-B-0 406 623 describes film-forming polyaspartic acid derivatives which are obtained by reacting polysuccinimide with amines and comprise structural units of the formula

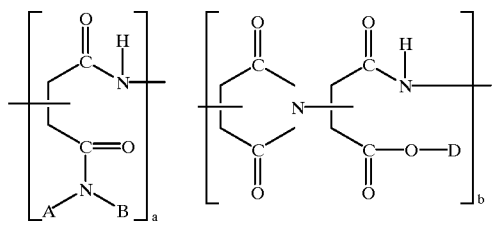

where
A=H or alkyl or alkylene of 1 to 8 carbons which can also be branched and can be substituted further by cycloaliphatic or aromatic radicals, in which case the cyclic substituent can also contain heteroatoms, or by R—O—groups, in which R=H or a linear or branched alkyl or cycloalkyl of 1 to 10 carbons,
B=H or an alkyl or alkylene radical as defined under A which can be identical to or different from A,
D=H or NH$_4$ or

where A and B are as defined above, or an alkali,
a=from 0.2 to 1 and
b=from 0.8 to 0,
which are used as coating materials and/or retardants for drug forms of therapeutic active substances and for foods and tobacco products. As the above formula shows, the monomer units, which are in salt form, are always attached to an imide monomer unit. The stoichiometric ratio of monomer units in salt form to imide monomer units is fixed at 1:1.

The cosmetic use of polyamino acids and their derivatives has also been described before. Polypeptides of protein hydrolysates, based for example on albumin or collagen, are obtainable commercially. For example, protein hydrolysates or partial hydrolysates of collagen having a molar weight from 1100 to 1300 and from about 8 to 14 monomer units and their sodium salts (e.g. Nutrilan® from Grunau) are used as protective colloids which are nonfoaming and have no washing action but possess dispersing and soil transport properties, for example in combination with surfactants. Similarly, various fatty acid-polypeptide condensation products are obtainable commercially as biodegradable anionic surfactants having good foaming and washing properties (e.g. Lamepon® from Grtnau).

DE-A-22 53 190 describes polyaspartic acid derivatives having acid amide residues and alkali metal carboxylate and/or alkaline earth metal carboxylate residues, their preparation by reacting polysuccinimide having a molecular weight from 300 to 30,000 with a primary or secondary amine and then hydrolyzing the product with an alkali metal or alkaline earth metal hydroxide or carbonate, and the use of the resulting products as surfactants and additives for detergents and cosmetics.

JP-A-0624 8072 describes the cosmetic use of polyaspartamides having alkali metal carboxylate residues.

In the field of cosmetology there is a great demand for water-soluble or -dispersible polymers having good biocompatibility, biodegradability and film-forming properties. Such film-forming polymers are used, for example, for setting and shaping the hair and improving its structure. The hair treatment compositions generally comprise a solution of the film former in an alcohol or in a mixture of alcohol and water and are sprayed is in the form, for example, of these aqueous-alcoholic solutions onto the hair. Following the evaporation of the solvent the hair is held in the desired shape at the points of mutual contact of the polymer which remains. The polymers should on the one hand be sufficiently hydrophilic that they can be washed out from the hair while on the other hand they should be hydrophobic, so that the hair treated with the polymers retains its shape even under conditions of high atmospheric humidity, with no sticking together of the individual hairs. To maximize the hairsetting effect, moreover, it is desirable to employ polymers having a relatively high molecular weight (K value>14 in accordance with E. Fikentscher, Cellulosechemie 13 (1932), pp. 58–64). However, owing to their high molecular weight, these polymers are generally more difficult to wash out.

The use of the polymers described above, based on polyamino acid derivatives, in cosmetology for setting, shaping and improving the structure of hair has not been described hitherto. Moreover, the known polymers do not fulfill the requirement of having good setting properties while nevertheless being easy to wash out.

It is an object of the present invention, therefore, to provide hair treatment compositions which on the one hand can be used as hairsetting products but on the other hand also possess improved washing-out properties (redispersibility).

We have found that this object is achieved by water-soluble or water-dispersible polyaspartic acid derivatives which are products of the reaction of polysuccinimide or polyaspartic acid with an amine mixture comprising at least one primary or secondary amine.

The present invention therefore provides for the use of water-soluble and/or water-dispersible polyaspartic acid derivatives on the basis of the units shown in the diagrammatic formula I

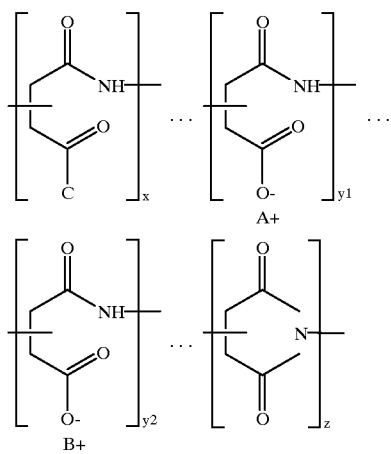

where
the sequence of the units is arbitrary,
the sum of x+y1+y2+z is 100, and
x is 30–100,
y1 is 0–70,
y2 is 0–50,
z is 0–30,
A is at least one primary or secondary nonaromatic amine,
B is at least one amine having a tertiary amino group, and
C is a radical derived from an amine of type A by elimination of an amine hydrogen,
or their carboxylic acid salts and polycarboxylic acid salts or quaternization products, in cosmetology, especially in hair cosmetology.

For the purposes of the present invention alkyl is straight-chain or branched. It is preferably straight-chain or branched $C_1$–$C_{30}$-alkyl, preferably $C_3$–$C_{10}$-alkyl, especially $C_4$–$C_8$-alkyl. Particular examples of alkyl are methyl, ethyl, propyl, 1-methylethyl, butyl, 1-methylpropyl, 2-methylpropyl, 1,1-dimethylethyl, n-pentyl, n-hexyl, ethylhexyl, n-heptyl and octyl.

The above comments regarding alkyl apply correspondingly to the alkyl part of alkoxy, alkoxycarbonyl and alkylaminocarbonyl.

Cycloalkyl is preferably $C_5$–$C_7$-cycloalkyl such as cyclopentyl, cyclohexyl or cycloheptyl. If substituted, cycloalkyl preferably has 1 or 2 substituents.

Cycloalkenyl is preferably $C_5$–$C_7$-cycloalkenyl such as cyclopentenyl, cyclohexenyl or cycloheptenyl. If substituted, cycloalkenyl preferably has 1 or 2 substituents.

Bicycloalkyl is preferably decalinyl, indanyl, hydrindanyl, bornyl, pinanyl, caranyl, norbornyl or bicyclo[2.2.2]octanyl.

Bicycloalkenyl can have one or two double bonds and is preferably indenyl, pinenyl, norbornenyl or norbornadienyl.

Aryl is preferably phenyl.

Hetaryl is preferably a 5- or 6-membered aromatic heterocycle containing 1 or 2 heteroatoms selected independently from N, O and S. In particular it is pyridyl, pyrimidinyl, pyrazinyl, thienyl, oxazolyl, imidazolyl, pyrrolyl or furyl.

Heterocyclyl is preferably a 5- to 7-membered saturated or unsaturated heterocycle containing 1, 2 or 3 heteroatoms selected independently from N, O and S. Where the heteroatom is nitrogen, this atom too, if desired, can be alkylated or acylated. Examples are pyrrolidinyl, imidazolidinyl, piperidyl and morpholinyl.

If substituted, aryl, hetaryl or heterocyclyl preferably has 1 or 2 substituents in any position(s).

The radical C is derived from an amine of type A from which an amine hydrogen has been eliminated in a condensation reaction to form an amide bond.

The radical $A^+$ is derived from an amine of type A which has formed an ammonium salt with a carboxyl.

The radical $B^+$ is derived from an amine of type B which has formed an ammonium salt with a carboxyl.

The terminal groups of polymers are residues having two free terminal carboxyls or one free terminal amino and one free carboxyl and also, if desired, their partial or complete quaternization products or, if desired, their salts with amines of type A or B or, if desired, their salts with carboxylic or polycarboxylic acids which are used for neutralization.

The amines A are preferably selected from
1) primary amines of formula II

where $R^1$ is
a) alkyl which can be substituted by 1, 2 or 3 groups selected independently from amino, hydroxyl, alkoxycarbonyl, alkylaminocarbonyl, cycloalkyl, cycloalkenyl, aryl or a 5- to 7-membered saturated, unsaturated or aromatic heterocycle containing 1, 2 or 3 N, S and/or O heteroatoms, where the cyclic radicals can additionally have 1, 2 or 3 substituents selected independently from alkyl, alkoxy, hydroxyl and hydroxyalkyl and/or the alkyl can be interrupted by 1, 2 or 3 nonadjacent oxygens;
b) cycloalkyl or cycloalkenyl each of which can be substituted by 1, 2 or 3 groups selected independently from alkyl, alkoxy, hydroxyl, hydroxyalkyl and —$COR^2$, where $R^2$ is alkyl, alkoxy or $NR^3R^4$ and where $R^3$ and $R^4$ independently are hydrogen or alkyl;
c) bicycloalkyl or bicycloalkenyl each of which can be substituted by 1, 2 or 3 of the possible substituents listed under b) for cycloalkyl and cycloalkenyl;
d) a 5- to 7-membered saturated heterocycle containing 1, 2 or 3 heteroatoms selected from O, N and S and possibly having 1, 2 or 3 substituents selected independently from alkyl, alkoxy, hydroxyl and hydroxyalkyl;
2) secondary amines of the formula III

where
$R^5$ and $R^6$ independently can be as defined for $R^1$, or
$R^5$ and $R^6$, together with the nitrogen to which they are attached, are a 5- to 7-membered saturated or unsaturated heterocycle possibly containing 1, 2 or 3 heteroatoms or hetero-groups selected independently from $NR^7$, $NCOR^7$, O and S, where $R^7$ is hydrogen or alkyl, and/or where the heterocycle can be substituted by 1, 2 or 3 substituents selected independently from alkyl, alkoxy, hydroxyl and hydroxyalkyl.

At least one of the amines A is preferably a primary amine of the formula II where $R^1$ is alkyl or cycloalkyl.

A is especially cyclohexylamine.

In accordance with a further preferred embodiment, at least one of the amines A is a primary amine of the formula II where $R^1$ is amino.

In that case, A is especially ethylenediamine.

According to a further preferred embodiment, at least one of the amines A is a primary amine of the formula II where $R^1$ is hydroxyalkyl.

In that case, A is, for example, pentanolamine, hexanolamine, heptanolamine or octanolamine.

According to yet another preferred embodiment, at least one of the amines A is a primary amine of formula II where $R^1$ is cycloalkylalkyl or arylalkyl.

In that case A is, for example, cyclopentylmethylamine, cyclohexylmethylamine or benzylamine.

At least one of the amines A is preferably a primary amine of the formula II, where $R^1$ is alkoxycarbonylalkyl.

In that case, examples of A are ethyl, propyl, butyl and tert-butyl alaninate, ethyl, propyl, butyl and tert-butyl valinate, ethyl, propyl, butyl and tert-butyl leucinate, ethyl, propyl and butyl glycinate, and especially tert-butyl glycinate.

According to another preferred embodiment, at least one of the amines A is a primary amine of the formula II where $R^1$ is alkylaminocarbonylalkyl.

In that case, A is, for example, the ethyl-, propyl-, butyl- or tert-butyl-carboxamides of the amino acids glycine, alanine, valine, leucine or isoleucine.

At least one of the amines A is preferably a secondary amine of the formula III where $R^5$ and $R^6$ independently are alkyl or cycloalkyl.

According to a further preferred embodiment, at least one of the amines A is a secondary amine of the formula III where $R^5$ is alkyl, cycloalkyl or hydroxyalkyl and $R^6$ is hydroxyalkyl.

In that case A is, for example, N-methylethanolamine, N-methylisopropanolamine, N-ethylethanolamine, N-ethylisopropanolamine, 2,2'-iminodiethanol or 2,2'-iminodipropanol.

According to yet another preferred embodiment, at least one of the amines A is a secondary amine of the formula III where $R^5$ and $R^6$, together with the nitrogen to which they are attached, are a 5- to 7-membered saturated heterocycle possibly containing a further heteroatom selected from S, O, $NR^7$ or $NCOR^7$, where $R^7$ is H, alkyl or hydroxyalkyl, and possibly containing in addition one or two substituents selected from alkyl and hydroxyl.

In that case A is preferably pyrrolidine, imidazolidine, piperidine, 4-methylpiperidine, 3-piperidinol, 4-piperidinol, morpholine, 2,6-dimethylmorpholine, piperazine, 1-methylpiperazine, 1-ethylpiperazine, N-(2-hydroxyethyl) piperazine, N-acylpiperazine and especially piperidine, morpholine or 1-methylpiperazine.

In a preferred embodiment use is made of polyaspartic acid derivatives for which the sum of the indices x+y1 in the diagrammatic formula I is 50 or more, preferably 75 or more, i.e. those having a corresponding number of radicals derived from amines of type A. Preference is also given to the use of derivatives for which the index y2 in the diagrammatic formula I is 5 or more, i.e. those having a corresponding number of radicals derived from amines of type B.

Suitable amines of type B are 1) tertiary amines of the formula IV $$NR^8R^9R^{10} \qquad (IV)$$

where $R^8$, $R^9$ and $R^{10}$ independently can be as defined for $R^1$, or $R^8$ and $R^9$, together with the nitrogen to which they are attached, are a 5- to 7-membered saturated or unsaturated heterocycle possibly containing 1, 2 or 3 heteroatoms selected from $NR^{11}$, $NCOR^{11}$ and O, where $R^{11}$ is hydrogen or alkyl, and/or possibly being substituted by 1, 2 or 3 substituents selected independently from alkyl, alkoxy, hydroxyl and hydroxyalkyl;

2) diamines of the formula V

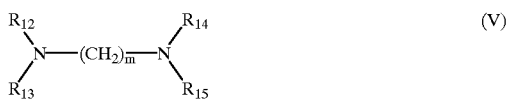

where m is an integer from 2 to 6, $R^{12}$ and $R^{13}$ independently are hydrogen or alkyl, $R^{14}$ and $R^{15}$ independently are alkyl or $R^{14}$ and $R^{15}$, together with the nitrogen to which they are attached, are a 5- to 7-membered saturated heterocycle having 1, 2 or 3 heteroatoms selected from N, O and S;

3) tertiary fatty amines of the formula VI

where p is an integer from 6 to 23, $R^{16}$ is hydrogen or the hydrocarbon radical of a saturated or unsaturated fatty acid, and $R^{17}$ and $R^{18}$ independently are alkyl.

In a preferred embodiment, at least one of the amines B is an amine of the formula IV where $R^8$ and $R^9$, together with the nitrogen to which they are attached, are a 5- to 7-membered saturated heterocycle possibly containing a further heteroatom selected from S, O, $NR^7$ and $NCOR^7$, where $R^7$ is H, alkyl or hydroxyalkyl, and possibly also containing one or two substituents selected from alkyl and hydroxyl.

In that case B is preferably N-methylpyrrolidine, N-methylpiperidine, N-methylpiperazine, N-ethylpiperazine, N,N'-dimethylpiperazine and, especially, N-methylpiperazine.

The molar proportion of quaternary ammonium groups in the polyaspartic acid derivatives of the formula I, expressed as the sum of y1+y2, is preferably 50% or more, in particular 70% or more. These derivatives are readily biodegradable.

In accordance with a specific embodiment use is also made, however, of polyaspartic acid derivatives with monomer units of the formula I, in which the sum y1+y2 is 0, i.e. which contain no quaternary ammonium groups.

To prepare polyaspartic acid derivatives with monomers units of the formula I in which y1+y2 is 0, the polysuccinimide or the polyaspartic acid is dissolved in an appropriate polar solvent, for example N-methlypyrrolidone, judiciously at elevated temperature, for example 100–130° C. To this solution there is then added an amine mixture containing at least one amine of the type A described above. The reaction is carried out in general at from 0° C. to 80° C. and for from 1 hour to several days. The product is then obtained in a customary manner, for example by precipitation with an organic solvent such as acetone.

The invention also provides water-soluble and/or water-dispersible polyaspartic acid derivatives on the basis of the units shown in the diagrammatic formula I

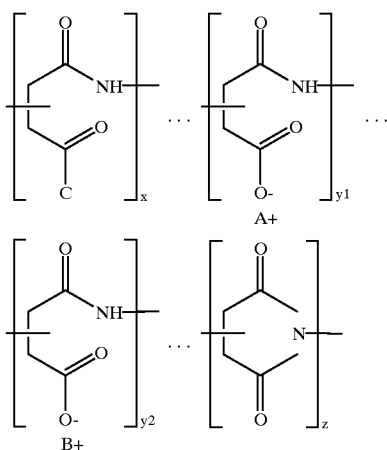

where the sequence of the units is arbitrary,
the sum x+y1+y2 +z is 100 and
x is 30–99.9,
y1 is 0.1–50,
y2 is 5–50,
Z is 0–30, and
A, B and C are as defined above,
or their carboxylic acid salts and polycarboxylic acid salts or quaternization products.

The novel polyaspartic acid derivatives are prepared by reacting polyaspartic acid or polysuccinimide with at least one amine of type A and at least one amine of type B in water as solvent. Where polysuccinimide is used to prepare the novel polyaspartic acid derivatives, it is preferably prepared by polycondensation of aspartic acid to give high molecular mass polysuccinimide with molecular weights of up to 100,000. The preparation takes place by known methods, for example by polycondensation in the presence of phosphoric acid as described, for example, by P. Neri et al. in J. Med. Chem. 16, (1973) 893.

To prepare the polyaspartic acid derivatives, the polysuccinimide or the polyaspartic acid is placed in water at from 20 to 70° C., for example. An amine mixture containing one amine of each of types A and B described above is added with stirring. Working judiciously under a nitrogen atmosphere, reaction is allowed to take place at from 30 to 100° C., preferably from 50 to 80° C., until the imide structure can virtually no longer be detected by IR spectroscopy. It is also possible, if desired, to raise the temperature and/or to remove excess amine (for example by distillation). The product can subsequently either be quaternized with a quaternizing agent such as dimethyl sulfate or neutralized with an acid or a polycarboxylic acid such as lactic acid or polyaspartic acid, respectively. The product can be obtained in solid form by spray drying or by precipitation with an organic solvent such as acetone.

In order to obtain polymers with good conditioning properties it is necessary for both amines of type A, some of which are preferably in salt form, and preferably tertiary amines of type B to be present in the polymer in order to achieve good biodegradability at the same time.

In accordance with an abovementioned preferred embodiment, however, polymers containing no ammonium salts are also used in cosmetology, preferably in hair cosmetology. The proportions of amides, salts and imides in the polymer can be controlled by way of the reaction conditions.

The novel water-dispersible compounds can be employed in the form of aqueous microdispersions having particle diameters of usually from 5 to 100 nm, in particular from 10 to 80 nm, and solids contents of usually from 0.1 to 40% by weight, in particular from 3 to 30% by weight. These microdispersions generally require no emulsifiers or surfactants for their stabilization.

Because of their ionic groups the polyaspartic acid derivatives are, in general, readily soluble in alcohol and water or are at least dispersible in alcohol and water without the aid of emulsifiers. Charged cationic groups can be produced from the tertiary amine nitrogens present by protonation, for example with alkylating agents such as $C_1$–$C_4$-alkyl halides or $C_1$–$C_4$-alkyl sulfates. Examples of such alkylating agents are ethyl chloride, ethyl bromide, methyl chloride, methyl bromide, dimethyl sulfate and diethyl sulfate.

In addition the aspartic acid derivatives can also, as mentioned, be converted by reaction with a mono- or polybasic carboxylic acid, for example lactic, citric or tartaric acid, etc., or by reaction with a polycarboxylic acid, such as polyaspartic acid, polyglutamic acid, carboxymethylcellulose, or polyacrylic acid, etc., into readily water- or alcohol-soluble or dispersible salts.

The novel polyaspartic acid derivatives are useful as auxiliaries in cosmetology and pharmacy and as coating materials for the textile, paper, printing and adhesive industries. They are particularly useful in hair cosmetology and pass readily onto the hair. For use as hair setting agents, preference is given to polyaspartic acid derivatives whose K value (in accordance with Fikentscher, Cellulose Chemie 13 (1932), pp. 58–64) is from 20 to 100.

The present invention also provides hair treatment compositions comprising the novel polyaspartic acid derivatives. In general, the composition comprises the polyaspartic acid derivatives in an amount of from about 0.1 to 30% by weight, based on the overall weight of the composition.

The novel hair treatment compositions are usually in the form of an aqueous dispersion or an aqueous-alcoholic solution. Examples of suitable alcohols are ethanol, propanol, isopropanol, etc. The compositions then comprise the polyaspartic acid derivative in an amount of from about 0.1 to 25% by weight, preferably from 1 to 15% by weight.

The novel hair treatment compositions also in general comprise customary cosmetic auxiliaries, for example plasticizers, such as glycerol and glycol, silicones, emollients, fragrances, UV absorbers, colorants, thickeners, antistats, combability improvers, preservatives and foam stabilizers.

If desired, the hair treatment compositions additionally comprise at least one conventional hairsetting polymer. The proportion by weight of polyaspartic acid derivative to the other hairsetting polymer is then, in particular, from 1:0.1 to 1:2. The hair treatment composition comprises the polymer mixture, in particular, in an amount of from 0.1 to 25% by weight, preferably from 1 to 15% by weight.

If the novel compositions are formulated as hair spray they comprise a sufficient amount of a propellant, for example a low-boiling hydrocarbon or ether, such as propane, butane, isobutane or dimethyl ether. Other propellants which can be used are compressed gases, such as nitrogen, air or carbon dioxide. The amount of propellant is kept as low as possible so as not to bring about an unnecessary increase in the VOC (VOC=volatile organic compounds) content. In general it is not more than 40% by weight, based on the overall weight of the composition.

The novel polyaspartic acid derivatives and compositions comprising them have the advantage that on the one hand they give the hair the desired strength and on the other hand the polymers are easier to wash out (more redispersible) than the prior art polymers. Furthermore, it is possible to prepare hair treatment compositions having a VOC content of less than 60% by weight and even purely aqueous formulations, even if they are formulated as hairsprays.

The intention of the nonlimiting examples given below is to illustrate the invention:

EXAMPLES

The K value was measured by the method of E. Fikentscher, Cellulose-Chemie 13 (1932), pp. 58–64 on a 1% strength solution in NMP having a pH of 7 and at 25° C.

a) Preparation Examples

Example 1: (Method A)

97 g of polysuccinimide are dissolved in 300 g of NMP (N-methylpyrrolidone) at room temperature under nitrogen in a three-necked flask fitted with stirrer, dropping funnel and reflux condenser. With gentle heating to about 30–40° C., 85 g (1 mol) of piperidine are slowly added dropwise at a pH of less than 9.2. The reaction mixture is stirred at about 20 to 40° C. for 16–20 hours. The NMP is then distilled off under reduced pressure at 120° C. to give an approximately 50% strength solution. The NMP solution is slowly added dropwise, with stirring, to 2000 ml of acetone. The precipitated product is filtered off with suction, washed 3 times with acetone and dried under reduced pressure at from 20 to 40° C. A white powder is obtained which is very readily soluble in water and in water/ethanol mixtures.

Examples 2 to 4 of Table 1 were prepared by a similar method.

Example 6: (Method B)

97 g of polysuccinimide in 400 g of water are charged to a three-necked flask fitted with stirrer, dropping funnel and reflux condenser. 109.1 g (1.1 mol) of cyclohexylamine are slowly added dropwise under nitrogen at a pH of less than 9.2 and at 60 to 70° C. The reaction mixture is then stirred at from 80 to 100° C. until the imide structure can virtually no longer be detected in the IR spectrum. The excess of amine is distilled off at 110° C. together with water, to give a 35 to 40% strength polyaspartic acid derivative solution.

Examples 5, 7 and 8 of Table 1 were prepared by a similar method.

TABLE 1

| Example No. | Si. mol | Pi. mol | Mo. mol | N-MPi. mol | Cha. mol | t-BG. mol | Eda. mol | K value (1% NMP) | Method |
|---|---|---|---|---|---|---|---|---|---|
| 1 | 1 | 1.0 | — | — | — | — | — | 23.0 | A |
| 2 | 1 | 0.7 | — | — | 0.3 | — | — | 24.1 | A |
| 3 | 1 | — | 1.0 | — | — | — | — | 23.4 | A |
| 4 | 1 | — | 0.7 | 0.3 | — | — | 0.03 | 27.3 | A |
| 5 | 1 | — | 0.7 | 0.3 | — | — | 0.03 | 25.4 | B |
| 6 | 1 | — | — | — | 1.1 | — | — | 23.2 | B |
| 7 | 1 | — | 0.7 | — | — | 0.35 | — | 22.6 | B |
| 8 | 1 | — | 0.5 | — | 0.5 | — | 0.03 | 25.4 | B |

Si.: Succinimide units in the polymer
Pi.: Piperidine
Mo.: Morpholine
N-MPi.: N-Methylpiperazine
Cha.: Cyclohexylamine
t-BG.: tert-Butyl glycinate
Eda.: Ethylene diamine
NMP: N-Methylpyrrolidone b) Use Examples

To demonstrate the use of the novel polyaspartic acid derivatives as hairsetting agents, the following formulations were prepared (VOC=volatile organic compounds):

A) VOC 80 Aerosol Hairspray:

| | |
|---|---|
| Polyaspartic acid derivatives 1–8 from Table 1 | 5% by weight |
| Ethanol abs. | 50% by weight |
| Water | 15% by weight |
| Dimethyl ether | 30% by weight |

B) VOC 55 Aerosol Hairspray:

| | |
|---|---|
| Polyaspartic acid derivatives 1–8 from Table 1 | 5% by weight |
| Ethanol abs. | 25% by weight |
| Water | 40% by weight |
| Dimethyl ether | 30% by weight |

C) VOC 55 Pump Spray:

| | |
|---|---|
| Polyaspartic acid derivatives 1–8 from Table 1 | 5% by weight |
| Ethanol abs. | 55% by weight |
| Water | 40% by weight |

The following performance properties were examined taking the abovementioned formulation A) as Example.
Curl Retention=Setting Effect on Strands of Hair in the Form of Locks at High Atmospheric Humidity (90%):

The Curl retention is the measure of the hairsetting effect. It is measured in a model test on locks of hair produced by a customary aqueous perm on hair about 15 cm in length, which was sprayed with formulation A) from a distance of 10 cm for 4 seconds. After the suspended locks had been treated for 5 hours in a climatically controlled chamber (25° C., 90% relative atmospheric humidity), the relative deformation (stretching) of the locks, based on the original shape, was determined. A high value denotes a high setting effect;

in other words, 100% would denote complete retention of the original form of the suspended locks, while 0% would denote fully stretched hair.

Flexural Strength

Measurement is carried out with 10 different strands of hair of approximately equal weight (2 g) and length (24 cm). The hair is mid-European brown hair. The strands of hair are placed for 1 hour in a solution of 50% ethanol and 50% water, then shampooed twice with Texapon® NSO solution (from Henkel KgaA) (10% solids) and rinsed with warm water at 40° C. The wet strands of hair are combed through and dried in air at room temperature. After drying, the strands of hair are weighed and are immersed in a solution of the formulation A), uniform distribution being ensured by multiple immersion and removal of the strands.

The excess solution is pressed off between thumb and forefinger and the hair is subsequently pressed carefully between filter paper to give a weight increase of from 0.4 to 0.5 g. The strands of hair are then shaped so that they have a circular cross-section. They are dried in a climatically controlled cabinet at 20° C. and 75% relative atmospheric humidity. After 12 hours, the strands are removed from the cabinet and subjected immediately to the hardness measurement. The strands of hair are placed on 2 cylindrical rolls (diameter 6 mm) which are arranged horizontally to one another at a distance of 9 cm. Exactly in the middle between the two points of contact, a cylindrical roll (diameter 6 cm) is pressed from above onto the strands of hair, with constantly increasing force, until the strands break. The force required to achieve breaking is measured. After the strand of hair has been broken it is released, as a result of which it stretches again. The force is then again increased continually until the strand breaks for a second time.

The results of performance testing are given in Table 2.

TABLE 2

Curl retention and flexural strength of formulation A)

| Example No. from Table 1 | Curl retention [%] | Flexural strength [cN] |
| --- | --- | --- |
| 1 | 63 | 107 |
| 2 | 68 | 103 |
| 3 | 71 | 115 |
| 4 | 45 | 118 |
| 5 | 39 | 82 |
| 6 | 52 | 100 |
| 7 | 38 | 98 |
| 8 | 55 | 109 |

As shown by Table 2, hair setting formulations containing the novel polyaspartic acid derivatives have a good setting effect.

We claim:

1. A water-soluble or water-dispersible polyaspartic acid on the basis of the units shown in the diagrammatic formula I

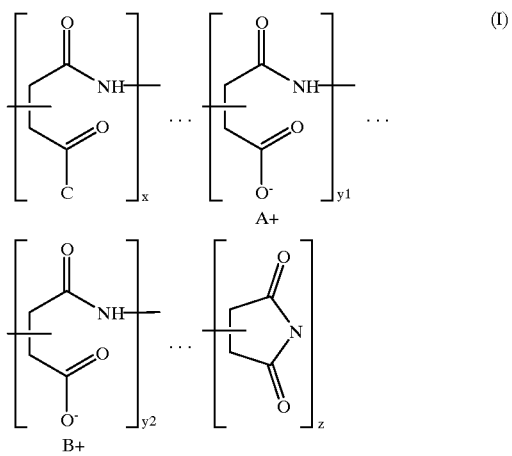

where the sequence of the units is arbitrary, the sum of $x+y1+y2+z$ is 100, and $x$ is 30–94.9, $y1$ is 0.1–50, $y2$ is 5–50, $z$ is 0–30, A is at least one primary or secondary non-aromatic amine, B is at least one amine having a tertiary amino group, and C is a radical derived from an amine of type A by elimination of an amine hydrogen, or a carboxylic acid salt or polycarboxylic acid salt or quarternization product thereof.

2. The polyaspartic acid defined in claim 1, where $z$ is 0–15.

3. The polyaspartic acid defined in claim 1, where the amine A is selected from 1) primary amines of the formula II

where $R^1$ is
  a) alkyl which may be substituted by 1, 2 or 3 groups selected independently from amino, hydroxyl, alkoxycarbonyl, alkylaminocarbonyl, cycloalkyl, cycloalkenyl, aryl or a 5- to 7-membered saturated, unsaturated or aromatic heterocycle containing 1, 2 or 3 hetero atoms selected from N, S and O, where the cyclic radicals may additionally have 1, 2 or 3 substituents selected independently from alkyl, hydroxyl and hydroxyalkyl, the alkyl may be interrupted by 1, 2 or 3 nonadjacent oxygens;
  b) cycloalkyl or cycloalkenyl each of which may be substituted by 1, 2 or 3 groups selected independently from alkyl, alkoxy, hydroxyl, hydroxyalkyl and —COR², where $R^2$ is alkyl, alkoxy or $NR^3R^4$ and where $R^3$ and $R^4$ independently are hydrogen or alkyl;
  c) bicycloalkyl or bicycloalkenyl each of which may be substituted by 1, 2 or 3 of the optional substituents listed under b) for cycloalkyl or cycloalkenyl;
  d) a 5- to 7-membered saturated heterocycle containing 1, 2 or 3 hetero atoms selected from O, N and S which may carry 1, 2 or 3 substituents selected independently from alkyl, alkoxy, hydroxyl and hydroxyalkyl;

2) secondary amines of the formula III

 (III)

where R⁵ and R⁶ independently can be as defined for R¹, or

R⁵ and R⁶, together with the nitrogen to which they are attached, are a 5- to 7-membered saturated or unsaturated heterocycle which may additionally contain 1, 2 or 3 hetero atoms or hetero-groups selected independently from NR⁷, N—COR⁷, O and S, where R⁷ is hydrogen, alkyl or hydroxyalkyl, and/or where the heterocycle may be substituted by 1, 2 or 3 substituents selected independently from alkyl, alkoxy, hydroxyl and hydroxyalkyl.

4. The polyaspartic acid defined in claim 3, where the amine A is selected from 1) primary amines of the formula II where R¹ is alkyl or cycloalkyl and the alkyl group may be substituted by alkoxycarbonyl or by a further amino;

2) secondary amines of the formula III, where R⁵ and R⁶, together with the nitrogen to which they are attached, are a 5- to 7-membered saturated or unsaturated heterocycle which may additionally contain 1, 2 or 3 hetero atoms or hetero-groups selected independently from NR⁷ and O, where R⁷ is hydrogen, alkyl or hydroxyalkyl.

5. The polyaspartic acid defined in claim 1, where the amine B is selected from 1) tertiary amines of the formula IV

 (IV)

where R⁸, R⁹ and R¹⁰ are selected from the group consisting of a) alkyl which may be substituted by 1, 2 or 3 groups selected independently from amino, hydroxyl, alkoxycarbonyl, alkylaminocarbonyl, cycloalkyl, cycloalkenyl, aryl or a 5- to 7-membered saturated, unsaturated or aromatic heterocycle containing 1, 2 or 3 hetero atoms selected from N,S and O, where the cyclic radicals may additionally have 1, 2 or 3 substituents selected independently from alkyl, hydroxyl and hydroxyalkyl and/or the alkyl may be interrupted by 1, 2 or 3 nonadjacent oxygens;

b) cycloalkyl or cycloalkenyl each of which may be substituted by 1, 2 or 3 groups selected independently from alkyl, alkoxy, hydroxyl, hydroxyalkyl and —COR², where R² is alkyl, alkoxy or NR³R⁴ and where R³ and R⁴ independently are hydrogen or alkyl;

c) bicycloalkyl or bicycloalkenyl each of which may be substituted by 1, 2 or 3 of the optional substituents listed under b) for cycloalkyl or cycloalkenyl;

d) a 5- to 7-membered saturated heterocycle containing 1, 2 or 3 hetero atoms selected from O, N and S which may carry 1, 2 or 3 substituents selected independently from alkyl, alkoxy, hydroxyl and hydroxyalkyl; or R⁸ and R⁹, together with the nitrogen to which they are attached, are a 5- to 7-membered saturated or unsaturated heterocycle which may additionally contain 1, 2 or 3 hetero atoms or hetero-groups selected independently from NR¹¹, N—COR¹¹ and O, where R¹¹ is hydrogen or alkyl, and/or where the heterocycle may be substituted by 1, 2 or 3 substituents selected independently from alkyl, alkoxy, hydroxyl and hydroxyalkyl, 2) diamines of the formula V

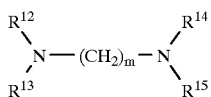 (V)

where m is an integer from 2 to 6,

R¹² and R¹³ independently are hydrogen or alkyl,

R¹⁴ and R¹⁵ independently are alkyl or R¹⁴ and R¹⁵, together with the nitrogen to which they are attached, are a 5- to 7-membered saturated heterocycle which may additionally contain 1, 2 or 3 hetero atoms selected from N, O and S, 3) tertiary fatty amines of the formula VI

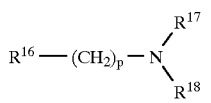 (VI)

where p is an integer from 6 to 23,

R¹⁶ is hydrogen or the hydrocarbon radical of a saturated or unsaturated fatty acid, and R¹⁷ and R¹⁸ independently are alkyl.

6. The polyaspartic acid defined in claim 1, where the sum of y1+y2 is 50 or more.

7. The polyaspartic acid defined in claim 1, having a K value of from 20 to 100.

8. A process for preparing a polyaspartic acid as defined in claim 1, which comprises reacting polyaspartic acid or polysuccinimide with at least one amine of type A and at least one amine of type B.

9. The process defined in claim 8, which further comprises reacting the polyaspartic acid with a quaternizing agent.

10. The process defined in claim 8, which further comprises reacting the polyaspartic acid with a carboxylic acid or polycarboxylic acid.

11. A hair treatment composition comprising at least one polyaspartic acid as defined in claim 1.

12. The hair treatment composition defined in claim 11 which comprises of from 0.1 to 25% by weight of the polyaspartic acid.

13. The hair treatment composition defined in claim 11 which comprises customary cosmetic auxiliaries selected from plasticizers, silicones, emollients, fragrances, TV absorbers, colorants, thickeners, antistats, combability improvers, preservatives and foam stabilizers.

14. The hair treatment composition defined in claim 11 which further comprises a different hairsetting polymer.

15. The hair treatment composition defined in claim 11 which is in the form of an aqueous dispersion or an aqueous-alcoholic solution.

16. The hair treatment composition defined in claim 15 in the form of a hair spray.

17. The polyaspartic acid defined in claim 1, where the sum of y1+y2 is 70 or more.

18. The hair treatment composition defined in claim 11 which comprises of from 0.1 to 15% by weight of the polyaspartic acid.

* * * * *

UNITED STATES PATENT AND TRADEMARK OFFICE
CERTIFICATE OF CORRECTION

PATENT NO.: 5,961,965

DATED: October 5, 1999

INVENTOR(S): KIM et al.

It is certified that error appears in the above-identified patent and that said Letters Patent is hereby corrected as shown below:

Col. 13, claim 5, line 45, delete "and/or".

Col. 13, claim 5, line 67, delete "and/or where".

Col. 14, claim 13, line 51, "TV" should be --UV--.

Signed and Sealed this

Second Day of May, 2000

Attest:

Attesting Officer

Q. TODD DICKINSON

Director of Patents and Trademarks